(12) United States Patent
Park et al.

(10) Patent No.: US 9,121,065 B2
(45) Date of Patent: Sep. 1, 2015

(54) NANOPARTICLE-OLIGONUCLEOTIDE HYBRID STRUCTURES AND METHODS OF USE THEREOF

(75) Inventors: So Jung Park, Wynnewood, PA (US); Xi-Jun Chen, Edison, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 126 days.

(21) Appl. No.: 13/814,652

(22) PCT Filed: Aug. 9, 2011

(86) PCT No.: PCT/US2011/047084
§ 371 (c)(1),
(2), (4) Date: Feb. 6, 2013

(87) PCT Pub. No.: WO2012/021516
PCT Pub. Date: Feb. 16, 2012

(65) Prior Publication Data
US 2013/0171646 A1    Jul. 4, 2013

Related U.S. Application Data

(60) Provisional application No. 61/371,994, filed on Aug. 9, 2010.

(51) Int. Cl.
| C12Q 1/68 | (2006.01) |
| C12N 15/00 | (2006.01) |
| C12N 15/74 | (2006.01) |
| C07H 21/02 | (2006.01) |
| C07H 21/04 | (2006.01) |
| C12N 15/10 | (2006.01) |
| C12N 15/87 | (2006.01) |

(52) U.S. Cl.
CPC .............. *C12Q 1/6876* (2013.01); *C12N 15/10* (2013.01); *C12N 15/87* (2013.01); *C12Q 1/6806* (2013.01); *C12Q 1/6816* (2013.01)

(58) Field of Classification Search
None
See application file for complete search history.

(56) References Cited

U.S. PATENT DOCUMENTS

| 5,229,320 A | 7/1993 | Ugajin |
| 5,482,890 A | 1/1996 | Liu et al. |
| 5,888,885 A | 3/1999 | Xie |
| 5,906,670 A | 5/1999 | Dobson et al. |
| 6,225,198 B1 | 5/2001 | Alivisatos et al. |
| 6,306,736 B1 | 10/2001 | Alivisatos et al. |
| 6,468,808 B1 | 10/2002 | Nie et al. |
| 2002/0160363 A1 | 10/2002 | McDevitt et al. |
| 2004/0033345 A1 | 2/2004 | Dubertret et al. |
| 2004/0067503 A1 | 4/2004 | Tan et al. |
| 2008/0274454 A1 | 11/2008 | Mirkin et al. |
| 2009/0322327 A1 | 12/2009 | Gao |

FOREIGN PATENT DOCUMENTS

WO   WO 2008/019142 A2 *   2/2008

* cited by examiner

*Primary Examiner* — James Martinell
(74) *Attorney, Agent, or Firm* — Mark S. Cohen; Pearl Cohen Zedek Latzer Baratz LLP

(57) ABSTRACT

The invention relates to hybrid structures comprising an amphiphilic nucleic acid-block co-polymer assembly on the exterior and a nanoparticle core, and methods of use thereof.

33 Claims, 13 Drawing Sheets

| No. Base Mismatch | DNA Sequence | |
|---|---|---|
| 0 | 3'Cy3-T₁₀TAGGAATAGTTATAA5' | Seq ID No: 4 |
| 1 | 3'Cy3-T₁₀TAGGAACAGTTATAA5' | Seq ID No: 5 |
| 2 | 3'Cy3-T₁₀TAGGAACGGTTATAA5' | Seq ID No: 6 |
| 3 | 3'Cy3-T₁₀TAGGAACGCTTATAA5' | Seq ID No: 7 |
| 25 | 3'Cy3-A₁₀CTGCCGGTTGCAAAG5' | Seq ID No: 8 |

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: oligonucleotide label

<400> SEQUENCE: 1
atccttatca atatt                                                    15

<210> SEQ ID NO 2
<211> LENGTH: 15
<212> TYPE: DNA
<213> ORGANISM: Artificial Sequence
<220> FEATURE:
<223> OTHER INFORMATION: oligonucleotide label

<400> SEQUENCE: 2
taggaatagt tataa                                                    15

<210> SEQ ID NO 3
<211> LENGTH: 15
<212> TYPE: DNA
<213> ORGANISM: Artificial Sequence
<220> FEATURE:

-continued

```
<223> OTHER INFORMATION: oligonucleotide label

<400> SEQUENCE: 3
atccttatca atatt                                                    15
```

NANOPARTICLE-OLIGONUCLEOTIDE HYBRID STRUCTURES AND METHODS OF USE THEREOF

CROSS-REFERENCE TO RELATED APPLICATIONS

This application is a National Phase Application of PCT International Application No. PCT/US11/47084, International Filing Date Aug. 9, 2011, claiming priority to U.S. Provisional Patent Application 61/371,994, filed Aug. 9, 2010, both of which are incorporated by reference herein in their entirety.

GOVERNMENT INTEREST

The work described herein was supported, in part, by Grant Number DMR 0847646 from the National Science Foundation. The United States government may have certain rights in the invention.

FIELD OF THE INVENTION

The invention relates to a hybrid structure comprising an amphiphilic nucleic acid-block co-polymer assembly on the exterior and a nanoparticle core, and methods of use thereof.

BACKGROUND OF THE INVENTION

Bioconjugates of inorganic nanoparticles have been extensively studied for various biological and medical applications such as bio-imaging and sensing, medical diagnostics, and drug delivery. In particular, gold nanoparticles heavily functionalized with thiol-modified oligonucleotides have shown great promise in DNA detection owing to their unusual DNA melting characteristics (i.e. sharp melting transitions and high binding constants) that originated from cooperative interactions of closely spaced DNA strands on the nanoparticle surfaces. Importantly, these unique properties have led to the development of DNA detection technologies with exceptionally high selectivity and sensitivity.

However, progress in extending these properties onto other types of nanoparticles has been hindered by the ability to obtain high density DNA on the surfaces of those nanoparticles. Accordingly, there exists a need for improved functionalization of nanoparticles.

SUMMARY OF THE INVENTION

The present invention relates to nanoparticle-amphiphilic oligonucleotide block co-polymer hybrid structures, and methods for making and using the same.

In one embodiment, the invention relates to a nanoparticle-nucleic acid hybrid structure, comprising a high density oligonucleotide-amphiphilic block co-polymer exterior assembly and a hydrophobic nanoparticle core.

In another embodiment, the invention relates to a method of enabling self-assembly of the hybrid structure provided herein, comprising the step of mixing a pre-determined amount of nucleic acid amphiphillic block-copolymer with a pre-determined amount of nanoparticles to enable the self-assembly of said hybrid structure.

In another embodiment, the invention relates to a method for transfecting a cell with a nucleic acid, comprising contacting a cell with the hybrid structure provided herein.

In another embodiment, the invention relates to a method for imaging a cell, comprising contacting a cell with the hybrid structure provided herein to provide a labeled cell, and imaging the labeled cell.

In another embodiment, the invention relates to method for detecting a complementary nucleic acid sequence with high selectivity, the method comprising the step of utilizing the hybrid structure provided herein in an assay to selectively detect said complementary nucleic acid.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
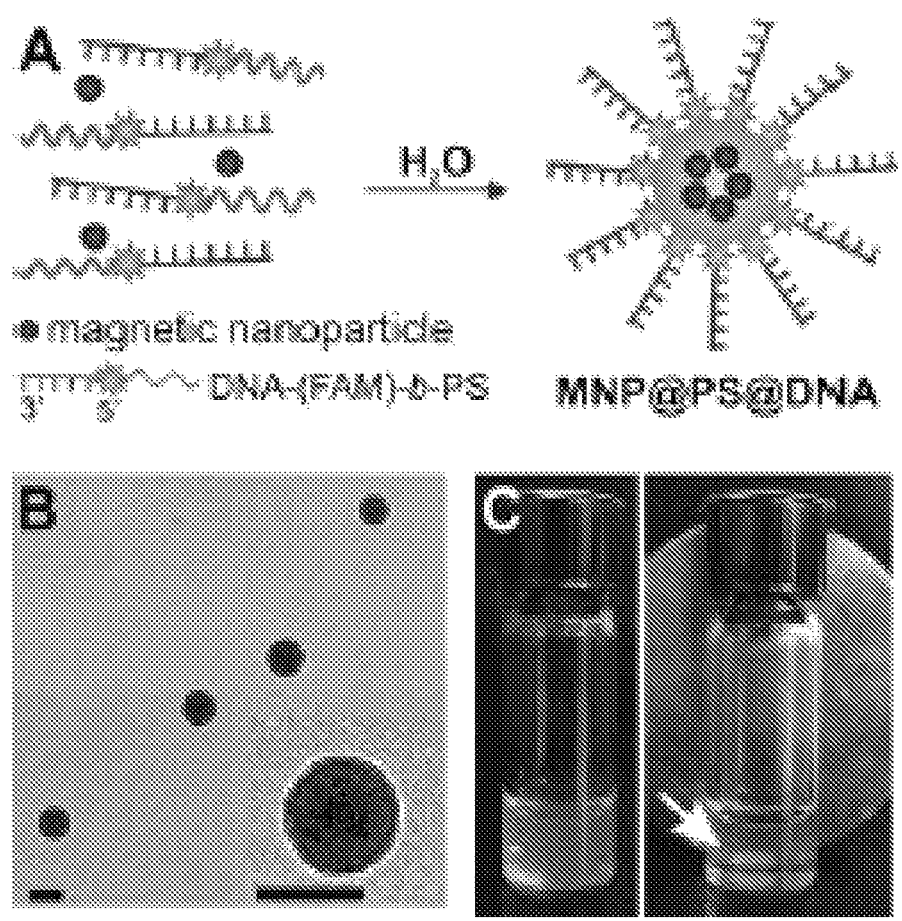
FIG. 1 shows (A) Schematic description for the preparation of DNA-b-PS assemblies incorporated with magnetic nanoparticles (MNP@PS@DNA). (B) A TEM image of MNP@PS@DNA. Inset: a high magnification TEM image showing incorporated magnetic nanoparticles. Scale bars=100 nm. (C) Pictures showing that MNP@PS@DNA can be collected with a magnet.

The invention relates in one aspect to a method of functionalizing nanoparticles with a high density nucleic acid layer, based on the self-assembly of nucleic acid block-co-polymers and nanoparticles (nanoparticle-nucleic acid hybrid structures). Nucleic acid block-copolymers are composed of an oligonucleotide strand operably (e.g., covalently) linked to another polymer, typically an organic polymer, and they self-assemble into various nanostructures in water due to their amphiphilicity.

In one aspect, the invention provides a nanoparticle-nucleic acid hybrid structures that includes a nanoparticle and a plurality of amphiphilic block co-polymers. In one related aspect hydrophobic magnetic nanoparticles are incorporated into the core of amphiphilic nucleic acid block-copolymer assemblies, resulting in nanoparticle/polymer hybrid particles with high nucleic acid density on their surfaces (FIG. 1A). Thus in the hybrid structures of the invention, the nanoparticle is encapsulated (e.g., belted) by the amphiphilic block-copolymer. Surprisingly, the self-assembled hybrid structure possesses extremely high binding capability to complementary nucleic acid even at very low salt concentrations, and they compete effectively with plain nucleic strands of the same sequence for the complementary nucleic acid. This unusual binding property makes these hybrid self-assemblies ideal candidates for, in one aspect, duplex DNA detection. Moreover, the hybrid nucleic acid/nanostructure recognizes complementary nucleic acid in high selectivity and can differentiate single base mismatches from complementary strands. This synthetic strategy can be extended to virtually any type of nanoparticles, and thus can be used to generate a wide range of multifunctional nanostructures with the extraordinary nucleic acid hybridization properties mentioned above. Through the selection and modification of the amphiphilic polymer, the hybrid structure can be functionalized for a desired purpose including, for example, therapeutic agent delivery and/or imaging.

The invention further relates to nanoparticle-nucleic acid hybrid structures, comprising a high density nucleic acid-amphiphilic block co-polymer exterior assembly and a hydrophobic nanoparticle core used to create a nucleic acid/nanoparticle hybrid structure with enhanced nucleic acid binding properties. In one aspect, the densely packed nucleic acid layer can increase the local DNA density and the local ion concentration, which enables the enhancement of DNA binding on the hybrid particles.

In another related aspect, the hybrid structure provided herein is highly selective as evidenced by its ability to enable detection of single base mismatches from complementary strands. Moreover, and in yet another related aspect, the hybrid structure provided herein enables selective nucleic acid binding to complementary nucleic acid under low salt concentration (see Example 3, below) and enhances the binding affinity of complementary nucleic acids.

In a related aspect, the nucleic acid on the hybrid structure selectively binds to complementary nucleic acid by detecting mismatches between the nucleic acid of the hybrid structure and nucleic acid contacted by the hybrid structure.

Any suitable nanoparticle, known to one of skilled in the art, can be used for the hybrid structure provided herein. Examples of a nanoparticle include, for example, but are not limited to, a gold nanoparticle, a magnetic nanoparticle, a semiconductor nanoparticle, an insulator nanoparticle, a metallic nanoparticle, a carbon black particle, a quantum dot, polymer nanoparticles, silica nanoparticles, and clusters and combinations thereof.

The nanoparticle can be a single color quantum dot, a multicolor quantum dot, or a combination of quantum dots (multiple single color quantum dots), which can be used to provide a multicolor combination. Suitable quantum dots include those known to those of skill in the art and include those that are commercially available. Other suitable quantum dots include those described in U.S. Pat. Nos. 5,906,670, 5,888,885, 5,229,320, 5,482,890, 6,468,808, 6,306,736, and 6,225,198, the description of these quantum dots and their preparations are incorporated herein by reference.

In one aspect, the nanoparticle is a magnetic nanoparticle selected from the group consisting of a metal nanoparticle, a metal oxide nanoparticle, a metalloid nanoparticle, a metalloid oxide nanoparticle, or a combination thereof. In yet another related aspect, the nanoparticle is an iron oxide magnetic particle. In another aspect, the iron oxide magnetic particle is functionalized via ligand exchange with alpha-carboxyl polystyrene. It is to be understood that the iron oxide magnetic particle can be functionalized through other means available in the art that enable the nanoparticle to be hydrophobic.

Combinations of nanoparticles (e.g., quantum dots and magnetic nanoparticles) can also be used to prepare the hybrid structures of the invention. To facilitate formation of the nanoparticle complexes of the invention and to provide an advantageous associative interaction with the amphiphilic polymer of the hybrid structure, the nanoparticles have a hydrophobic surface. The hydrophobic surfaces can be prepared by coating the nanoparticle with a hydrophobic ligand. Suitable hydrophobic surfaces include surfaces having hydrocarbon components. For example, the nanoparticle can be a hydrophobic ligand coated nanoparticle (e.g., quantum dot or magnetic particle).

The nanoparticles used in the present invention can vary in size, as would be understood by a skilled artisan, and include but are not limited to, a size ranging 1-1000 nanometers in diameter, from 1-500 nanometers in diameter, 1-250 nanometers in diameter, 1-100 nanometers in diameter, 1-50 nanometers in diameter, 1-10 nanometers in diameter.

In addition to including a nanoparticle, the hybrid structures of the invention include an amphiphilic polymer having a plurality of hydrophobic moieties, which advantageously interact associatively with the nanoparticles having a hydrophobic surface, and a plurality of amine moieties, which advantageously reversibly associate nucleic acids to the hybrid structure by electrostatic interactions. The hydrophobic segments can include hydrocarbon moieties (linear, branched, or cyclic) or aromatic moieties (e.g., phenyl). In one embodiment, the amphiphilic polymer is an amphiphilic alternating copolymer. In another embodiment, the amphiphilic polymer is an amphiphilic random copolymer. In a further embodiment, the amphiphilic polymer is an amphiphilic block co-polymer. In a related aspect, the nanoparticle and the oligonucleotide-amphiphilic block co-polymer self assemble to form the hybrid structure provided herein. In another related aspect, the block-copolymers of the present invention comprise an oligonucleotide block and a polystyrene block.

Suitable amphiphilic polymers useful in the complexes of the invention can be prepared by chemical modification of suitable polymers. For example, suitable amphiphilic polymers can be prepared by grafting or otherwise reacting functional groups on the polymer with suitable compounds to incorporate groups having the desired functionality (e.g., hydrophobic, amine, and other functional group) into the polymer. Alternatively, suitable amphiphilic polymers useful in the complexes of the invention can be prepared by polymerization or copolymerization of suitable monomers. For example, an amphiphilic polymer can be prepared by copolymerizing a hydrocarbon-containing monomer and an amine-containing monomer to provide a copolymer having a plurality of hydrocarbon moieties and a plurality of amine moieties. Suitable random, block, and alternating copolymers can be prepared by conventional polymerization techniques. When it is desired to include additional functionality to the polymer, additional comonomers (e.g., carboxylic acid- or ester-containing monomers) can be included in the polymerization to provide amphiphilic polymers having, in addition to the hydrophobic and amine moieties, other functional groups (e.g., carboxylic acid groups).

The other functional groups can be incorporated into the polymer for a variety of purposes. For example, carboxylic acids groups (e.g., carboxylic acid groups having pKa of from about 5 to about 7) can be incorporated into the polymer to impart the polymer with the ability to travel through physiological pH environments as salts and then disrupt cellular membranes in acidic environments (e.g., carboxylic acid group protonation to affect endosomal membrane disruption at endosomal pH, about pH 5) to enhance delivery of the complex and its associated nucleic acid into the cytosol. Carboxylic acids groups and other neutral groups can be included in the polymer to reduce the binding affinity of the associated nucleic acid, as desired. Carboxylic acid groups and other groups can also be included in the polymer so as to provide sites for polymer crosslinking or sites for tethering other functional molecules, such as targeting agents.

The amphiphilic polymer's amine moiety is effective for associating nucleic acids to the hybrid structure. Representative amine groups useful for incorporation into the amphiphilic polymer (and hybrid structure of the invention) include primary amine groups, secondary amine groups, tertiary amine groups, quaternary amines group, and combinations of these amine groups. In one embodiment, the amine moiety is a dimethyl amino group. For nucleic acid delivery, in one embodiment, the amphiphilic polymer includes a plurality of amine moieties and the hybrid structure has a positive zeta potential. In certain embodiments, the hybrid structure has a zeta potential from about 10 to about 50 millivolt.

The amine moiety can be incorporated into the amphiphilic polymer by conventional chemical methods. As noted above, polymers containing amine moieties can be prepared by polymerization using an amine-containing monomer. Alternatively, a polymer have a suitable functional group (e.g., carboxylic acid anhydride or carboxylic acid group) can be reacted with a suitable compound (e.g., alcohol or amine compound bearing an amine moiety) to provide a polymer having a plurality of amine moieties, as pendant moieties, covalently coupled to the polymer (e.g., ester or amide bonds).

In one aspect, the amphiphilic polymer includes a hydrocarbon moiety. In another aspect, the hydrocarbon moiety can include an alkyl, an aryl moiety, or an aralkyl moiety. Suitable alkyl moieties include linear, branched, and cyclic alkyl moieties (e.g., C1-24 moieties). Representative alkyl moieties include C1-C24 n-alkyl moieties. In one embodiment, the alkyl moiety is a C8-C16 n-alkyl moiety. In one embodiment, the alkyl moiety is a C8-C12 n-alkyl moiety.

In one aspect, the amphiphilic polymer is an amphiphilic alternating copolymer. Suitable amphiphilic alternating copolymers include hydrophilic carboxylic acid moieties, hydrophobic hydrocarbon moieties, and amine moieties. A representative amphiphilic alternating copolymer useful in the invention is a poly(maleic anhydride-alt-1-decene) modified with dimethylaminopropylamine (PMAL).

Suitable amphiphilic polymers have an average molecular weight of from about 500 to about 5,000,000 g/mole. In one embodiment, the amphiphilic polymer has an average molecular weight of from about 5,000 to about 500,000 g/mole.

In certain embodiments, the hybrid structures of the invention further include a targeting agent. As used herein, the term "targeting agent" refers to a chemical moiety associated with (e.g., covalently coupled or otherwise stably associated with) the hybrid structures that direct the hybrid structures to a specific site where the hybrid structures can to then be imaged or where the hybrid structures delivers its associated therapeutic agent. Suitable targeting agents include those known in the art. Representative targeting agents are one of a binding pair. In one embodiment, the targeting agent is an antibody or fragment thereof or its antigen. The antigen can be a small molecule, peptide, protein, polynucleotide, or polysaccharide. In one embodiment, the targeting agent is a nucleic acid or its complement. The nucleic acids can be DNAs and RNAs. In one aspect, the targeting agent is an enzyme or its substrate. In one embodiment, the targeting agent is a receptor or its ligand. In another aspect, the targeting agent is a nucleic acid or its partner protein. In yet another aspect, the targeting agent is a ligand for a cell, a cell membrane, or an organelle.

The hybrid structure described herein, further includes associated nucleic acids. In this aspect, the nucleic acids are associated to the hybrid structure through an electrostatic interaction with the amphiphilic polymer's pendant positively charged groups (e.g., amine groups).

In one aspect, the nucleic acid is a nucleic acid analog, or a nucleic acid mimic. Representative nucleic acids, analogs, and mimics that are advantageously included in a hybrid structure provided herein include RNAs, chemically modified DNAs or RNAs, siRNA, RNA analogs, and RNA mimics, and single or doubled stranded DNAs, DNA analogs, oligonucleotides and DNA mimics or combinations thereof. In another aspect the oligonucleotide is an oligonucleotide ranging in size from 5-50 base pairs. In another aspect of the present invention the oligonucleotide ranges in size from 5-100 base pairs, from 5-200 base pairs, from 5-300 base pairs, or from 5-500 base pairs as would be understood by a skilled artisan.

In a related aspect, the term "nucleic acid analog" or "nucleic acid mimic" refers to a nucleic acid (DNA or RNA) that is structurally similar to the native nucleic acid, but differs from the native nucleic acid (e.g., through chemical modification) at one or more of the nucleic acid backbone (e.g., phosphate in native nucleic acids), nucleic acid sugar (e.g., deoxyribose for native DNA and ribose in native RNA), and nucleic acid base (e.g., adenosine, cytosine, guanine, thymidine, or purine in native nucleic acids.) Nucleic acid analogs and mimics commonly result from modifications of native nucleic acids at the nucleobase (e.g., modified base), the sugar (e.g., fluorinated or deoxy sugars), and/or the phosphodiester backbone (e.g., peptide or thioester backbones). Nucleic acid analogs and mimics are known to those of skill in the art and include, for example, locked nucleic acids (LNAs), peptide nucleic acids (PNAs), and morpholinos. LNAs, PNAs, and morpholinos can form both duplexes and triplexes, have improved biostability compared to native nucleic acids, and have become a versatile tool for DNA and RNA recognition. LNAs are commonly used for specific, high-affinity recognition of single-stranded DNA (ssDNA) and single-stranded RNA (ssRNA). LNAs are also used in therapeutic and diagnostic applications. PNAs are a type of DNA analog having neutral charge. PNAs are extreme stable making them ideal candidates for antisense and antigen applications. Morpholino analogs overcome the problems associated with the high cost of other DNA analogs and are an important knockdown tool in developmental biology due to its ability for cytosolic delivery in embryos by microinjection. Nucleic acid analogs provide an advantage to therapeutic and diagnostic applications limited by the instability of native nucleic acids in these applications.

Representative nucleic acids and analogs useful in the hybrid structures of the invention include therapeutic nucleic acids and therapeutic nucleic acid analogs and mimics.

In another aspect, the invention provides a composition containing a hybrid structure of the invention and an acceptable carrier or diluent. For therapeutic and/or diagnostic applications, in which the composition is administered to a subject in need thereof, the composition includes a pharmaceutically acceptable carrier or diluent. The composition can be administered parenterally, for example, orally, transdermally (e.g., patch) intravenously (injection), intraperitoneally (injection), and locally (injection).

In another aspect of the invention, methods for making the hybrid structures are provided. In a related aspect, provided herein is a method of enabling self-assembly of the hybrid structure of the present invention. The process comprises, in one aspect, the step of mixing a pre-determined amount of nucleic acid amphiphillic block-copolymer with a pre-determined amount of nanoparticles to enable the self-assembly of said hybrid structure. It is to be understood by a skilled artisan that a "pre-determined amount" can be empirically determined. In another embodiment, the method of self-assembling the hybrid structures of the present invention is detailed in the Examples section herein below.

In one related aspect, the hybrid structure provided herein comprises a fluorescence molecule that enables, for example, target interaction or binding analysis, or imaging analysis, or any other technique known in the art that makes use of fluorescence markers as would be understood by a skilled artisan. In another related aspect, the fluorescence molecule is a fluorescein dye, a cyanine dye, a combination thereof or any such molecule used in the art for fluorescence detection.

The hybrid structures of the invention can be used to image cells. In these methods, cells are contacted with a hybrid structure of the invention including an associated nucleic acid to provide labeled cells (i.e., cells containing the hybrid structures or having the hybrid structures otherwise associated thereto). The labeled cells can then be imaged. Labeled cells can also be tracked by imaging (e.g., real-time imaging). For example, tumor cells or stem cells can be effectively labeled by the hybrid structures of the invention, imaged, and their migration tracked by further subsequent imaging. For hybrid structures that include quantum dots as nanoparticles, the hybrid structures can be used to fluorescently image cells labeled with the hybrid structure of the invention. For hybrid structures that include magnetic nanoparticles, the hybrid structures can be used to magnetically resonance image cells labeled with the hybrid structure of the invention. Cells labeled with any of the hybrid structures of the invention can also be imaged by electron microscopy (e.g., TEM). The hybrid structures of the invention allow for real-time imaging. As noted above, the cell can be contacted with a composition that includes the hybrid structure. In certain embodiments, the hybrid structure can further include a targeting agent to direct the hybrid structure to a cell of interest. Imaging can include whole body imaging as well as ex vivo imaging (e.g., tissues).

In a related aspect, provided herein is a method for transfecting a cell with a nucleic acid, comprising contacting a cell with the hybrid structure of the present invention, where the hybrid structure further comprises a targeting agent. In another related aspect, the method comprises contacting the cell with the hybrid structure in the presence of an applied magnetic field.

In one aspect, the hybrid structure of the present invention is useful in various medical applications such as magnetic resonance imagining (MRI), local drug delivery, and treatment of diseases by magnetic hyperthermia therapy. Magnetic hyperthermia is based on the fact that magnetic nanoparticles, when subjected to an alternating magnetic field, produce heat. As a consequence, if magnetic nanoparticles are put inside, for example, a tumor and the whole patient is placed in an alternating magnetic field of well-chosen amplitude and frequency, the tumor temperature would raise. This could kill the tumor cells by necrosis if the temperature is above 45° C., or could improve the efficiency of chemotherapy if the temperature is raised at about 42° C. Therefore, in a related aspect, provided herein is a method of treating a disease by magnetic hyperthermia therapy where the method comprises the step of contacting a cell associated with a disease with the hybrid structure of the present invention, where the hybrid structure further comprises, in one aspect, a targeting agent. In another related aspect, the method comprises the step of contacting the cell with the hybrid structure in the presence of an applied magnetic field. In one aspect, the disease is a cancer and the cell is a tumor.

In a related aspect also provided herein is a method of separating nucleic acid molecules, the method comprising the step of contacting a nucleic said molecule complementary to said nucleic acid molecule comprised by the hybrid structure provided herein. The method further comprises the step of contacting the nucleic acid with the hybrid structure in the presence of an applied magnetic field.

In a related aspect, provided herein is a method for imaging a cell, the method comprising the step of contacting the cell with the hybrid structure of provided herein to provide a labeled cell, and imaging the labeled cell. The imaging can be optical imaging and can comprise fluorescence imaging, scattering imaging, colorimetric imaging, electron microscopy imaging, or magnetic resonance imaging. In another related aspect, the hybrid structure comprises a quantum dot and the imaging comprises fluorescence imaging. In another related aspect, the hybrid structure comprises a magnetic nanoparticle and the imaging comprises magnetic resonance imaging.

The invention also provides, in a related aspect, a method for detecting a complementary nucleic acid sequence with high selectivity in solution, the method comprising the step of utilizing the hybrid structure provided herein in an assay to selectively detect a complementary nucleic acid. In another related aspect, the selection process comprises an assay, where such assay can be a nucleic acid binding assay that detects binding of the nucleic acid of the hybrid structure to a complementary nucleic acid. The hybrid structure provided herein unexpectedly enables detection of a complementary nucleic acid under low salt concentrations. The hybrid structure provided herein also shows the ability to differentiate or detect single base mismatches from complementary strands. In current methods, the solution containing duplex DNA is heated to dissociate the duplex DNA. Therefore, the hybrid structure provided herein can be used to detect the presence or absence of single strand of a gene or nucleic acid, or oligonucleotide with high selectivity and sensitivity. The hybrid structure provided herein can also be used to detect the presence or absence of a duplex DNA, gene, nucleic acid, or oligonucleotide with high selectivity.

In another aspect, provided herein is a method for detecting the level of expression of a complementary nucleic acid sequence in a sample, the method comprising the step of utilizing the hybrid structure provided herein in an assay to detect the level of expression of said complementary nucleic acid.

In another aspect, provided herein is a method for detecting a polymorphism associated with a complementary nucleic acid sequence in a sample, the method comprising the step of utilizing the hybrid structure provided herein in an assay to detect said polymorphism associated with said complementary nucleic acid. In one embodiment, the polymorphism is a single nucleotide polymorphism (SNP).

In another aspect, provided herein is a method for detecting one or more base mismatches in a complementary nucleic acid sequence in a sample, the method comprising the step of utilizing the hybrid structure provided herein in an assay to detect said one or more base mismatches in said complementary nucleic acid. The detection of nucleic acid described herein can be accomplished by any means or methods, known to one of skilled in the art, for example, but not limited to, polymerase chain reaction (PCR), microarrays, and in situ hybridization.

Analysis of detection of base mismatches by the hybrid structures provided herein can be accomplished by any means and methods known in the art, including, but not limited to Fluorescence Energy Resonance Transfer (FRET), as demonstrated in the Examples below.

In one aspect, the methods provided herein strategy can be extended to make multifunctional nanoparticles with various types of nanoparticles and small molecules.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Synthesis of DNA-b-PS

Block-copolymers composed of an oligonucleotide block and a PS block were synthesized by coupling phosphoramidite-modified PS (Mn=10.4 Kg/mol) to oligonucleotides grown on glass beads, following modified literature procedures. In a typical experiment, hydroxyl terminated-polystyrene (4.16 g, 0.4 mmol) was first prepared by reversible addition-fragmentation chain transfer (RAFT) polymerization with a random incorporation of approximately one anthracene-acrylate per chain. To prepare phosphoramidite-modified PS, synthesized hydroxyl terminated-polystyrene was added in solid form to a three-neck round bottom flask with magnetic stiffing bar. The reaction flask was vacuumed and purged with $N_2$; the process was repeated three times. With stirring, anhydrous dichloromethane (15 mL), chlorophosphoramidite (0.11 mL, 0.0048 mmol) and anhydrous diisopropylethylamine (0.12 mL) were added to the reaction flask. The solution was then stirred for two hours. The resulting solution was washed with $Na_2CO_3$ and brine consecutively and dried over $MgSO_4$. The product was further dried in rotoevaporator to yield 3.3 g of sticky yellow solids of phosphoramidite-modified PS (80% yield).

The synthesized phosphoramidite-modified PS was coupled to DNA by the syringe synthesis. A 10 µmol scale synthesis of oligonucleotide strand 5'-FAM-$A_{10}$ATCCTTAT-CAATATT-3' (SEQ ID NO: 1) was carried out using standard solid state DNA synthesis. Phosphoramidite-modified PS was dissolved in anhydrous dichloromethane (20 mL, 500 mol) and activated with a 0.5 M tetrazole activator solution (3 mL, 1.5 mmol). The CPG beads containing DNA were added to the activated phosphoramidite-modified PS and the mixture was stirred overnight under argon. Then, the CPG beads were washed rigorously with anhydrous dichloromethane to remove unconjugated PS. The DNA-b-PS was deprotected and cleaved from the solid support, i.e. CPG beads, by incubating the beads in concentrated ammonia at 55° C. for 16 h. The CPG beads were washed with purified water to remove unconjugated DNA. The DNA-b-PS was then recovered by washing the beads with DMF. The presence of both PS and DNA was confirmed by the photoluminescence of anthracene and fluorescein tags. The synthesis yielded 3 umol of DNA-b-PS (30% yield).

Preparation of Polystyrene (PS)-Modified Magnetic Nanoparticles (MNP)

Typically, oleic acid-stabilized MNPs (5.0±0.3 nm, 50 μg/mL in chloroform ($CHCl_3$), 50 μL) was mixed with α-carboxyl polystyrene (Mw=11,247 g/mol, 10 mg/mL in $CHCl_3$, 100 μL). The solution was left to stand on the bench top overnight. The resulting PS-modified MNPs were precipitated with acetone and collected by centrifugation (7K, 15 min). The purified PS-modified MNP was redispersed in dimethylformamide (DMF).

Preparation of DNA-b-PS Assemblies Incorporated with MNPs (MNP@PS@DNA)

A DMF solution of DNA-b-PS (10 μM, 300 μL) was mixed with a DMF solution of PS-modified MNPs (50 μg/mL, 10 μL) in a scintillation vial with stiffing. The solution was then further diluted with 1 mL of DMF. Purified water (18.0 MΩ) was slowly added to the solution at a rate of 10 μL per every 30 seconds for a period of 15 minutes to induce the self-assembly of amphiphilic DNA-b-PS and nanoparticles. The solution was left stiffing overnight. Then, 1 mL of water was slowly added to the mixture at a rate of 1 drop per every 30 seconds. The solution was then dialyzed overnight in water. The resulting DNA-b-PS assemblies incorporated with MNPs (MNP@PS@DNA) are dispersed in water or a buffer solution after centrifugation and purification by a magnet.

Example 1

Synthesis of Amphiphilic Block-Copolymers

In typical experiments, amphiphilic block-copolymers composed of an oligonucleotide block and a polystyrene block (DNA-b-PS) were synthesized by coupling phosphoramidite-modified PS (Mn=10.4 Kg/mol) to oligonucleotides grown on controlled pore glass (CPG) beads. To monitor DNA hybridization properties (vide infra), fluorescein (FAM) was inserted in-between DNA and PS by attaching FAM at the 5' end of DNA. PS-modified iron oxide magnetic nanoparticles (MNP) were prepared from oleic-acid stabilized MNPs (diameter: 5.0±0.3 nm) via ligand exchange with α-carboxyl PS. DNA block-copolymers and nanoparticles were self-assembled by first mixing them in a relatively good solvent (i.e. DMF), followed by the slow addition of water to the mixture and overnight dialysis in water (FIG. 1). The prepared hybrid particles of block-copolymers and magnetic nanoparticles (MNP@PS@DNA) were collected by centrifugation or by using a magnet (FIG. 1C), and transferred to phosphate buffer solutions (pH 7) or water. The self-assembling process resulted in the incorporation of iron oxide nanoparticles in the core of the assemblies, which are surrounded by a dense layer of DNA (FIG. 1A). A representative transmission electron microscope (TEM) image of the assemblies is presented in FIG. 1B. The diameter of the assemblies was measured to be 113±15 nm by TEM, and the to hydrodynamic diameter obtained by dynamic light scattering (DLS) measurements was 161±8 nm. The exact composition of the hybrid particle's core can be more complex than that of a simple micelle incorporating nanoparticles, and is likely to encapsulate a small amount of residual PS homopolymers or reverse micelles of block-copolymers along with magnetic nanoparticles.

Example 2

DNA Hybridization Properties of Hybrid Particles of Block-Copolymers and Magnetic Nano Particles (MNP@PS@DNA)

Figure 2:
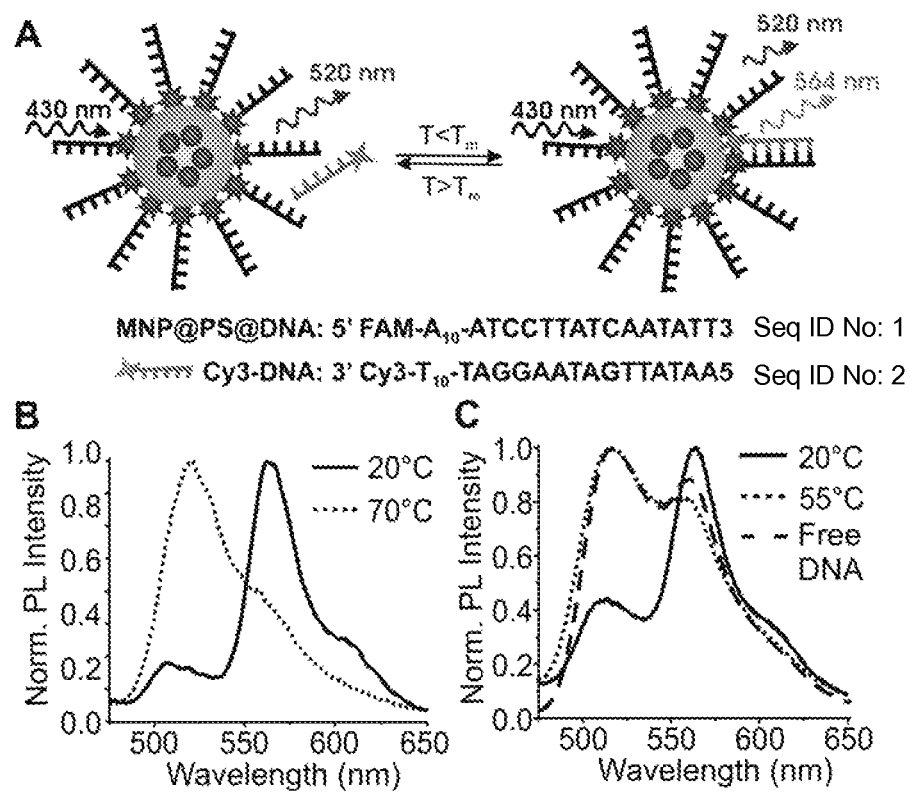
FIG. 2 shows (A) Schematic description for the binding of Cy3-labeled complementary DNA (Cy3-DNA) to MNP@PS@DNA below DNA melting temperature (B) Fluorescence spectra of MNP@PS@DNA mixed with Cy3-DNA in 0.3 M PBS below (solid) and above (dotted) DNA melting temperature. (C) Fluorescence spectra of MNP@PS@DNA mixed with Cy3-DNA in water with no added salt below (solid) and above (dotted) DNA melting temperature. For comparison, a fluorescence spectrum of plain FAM-modified DNA mixed with the complementary Cy3-DNA in the same condition was collected at 20° C. (dashed), which reveals negligible FRET. For all spectra, the excitation wavelength was 430 nm, which selectively excites FAM.

Properties of MNP@PS@DNA were evaluated by hybridizing Cy3-modified complementary target DNA (Cy3-DNA: 3' Cy3-$T_{10}$-TAGGAATAGTTATAA5') (SEQ ID NO: 2) to the FAM-modified DNA (5'FAM-$A_{10}$-ATCCTTATCAATATT3') (SEQ ID NO: 1) on MNP@PS@DNA (FIG. 2). DNA hybridization events were monitored by measuring the Förster resonance energy transfer (FRET) between FAM on MNP@PS@DNA and Cy3 on Cy3-DNA (FIG. 2A). FIG. 2B presents fluorescence spectra of 0.3 M phosphate buffered saline solution (PBS, pH 7, 10 mM phosphate buffer, 0.3 M NaCl, 800 μL) containing MNP@PS@DNA ([DNA-b-PS]: 200 pmol) and Cy3-DNA (800 pmol), taken with 430 nm excitation where Cy3 does not absorb strongly. As Cy3-DNA binds to MNP@PS@DNA, Cy3 fluorescence intensity (564 nm) increases relative to that of FAM (520 nm) due to energy transfer from FAM to Cy3 (FIG. 2B, solid). The FRET efficiency ($E_{FRET}$) of the sample was determined to be 76.8±1.6% by comparing the fluorescence intensity of the donor with and without the acceptor. The spectral change due to FRET was reversible. As the temperature increases above the DNA melting temperature, Cy3-DNA dehybridizes from MNP@PS@DNA resulting in the recovery of FAM fluorescence (FIG. 2B, dotted). This temperature dependence confirms that the FRET observed at room temperature is due to specific DNA interactions between MNP@PS@DNA and the complementary target DNA.

Figure 6:
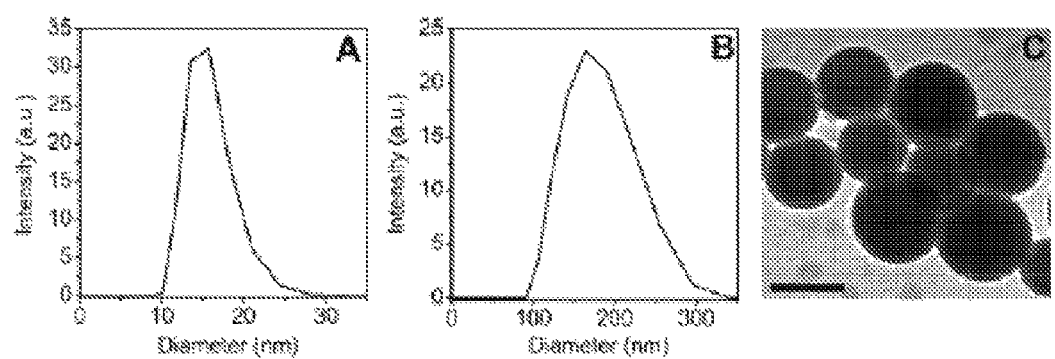
FIG. 6 shows DLS measurements of simple micelles of (A) DNA-b-PS (PS@DNA) and (B) DNA-b-PS assemblies encapsulating PS homopolymers (PS@PS@DNA). (C) A TEM image of PS@PS@DNA. Scare bar=250 nm.
Figure 7:
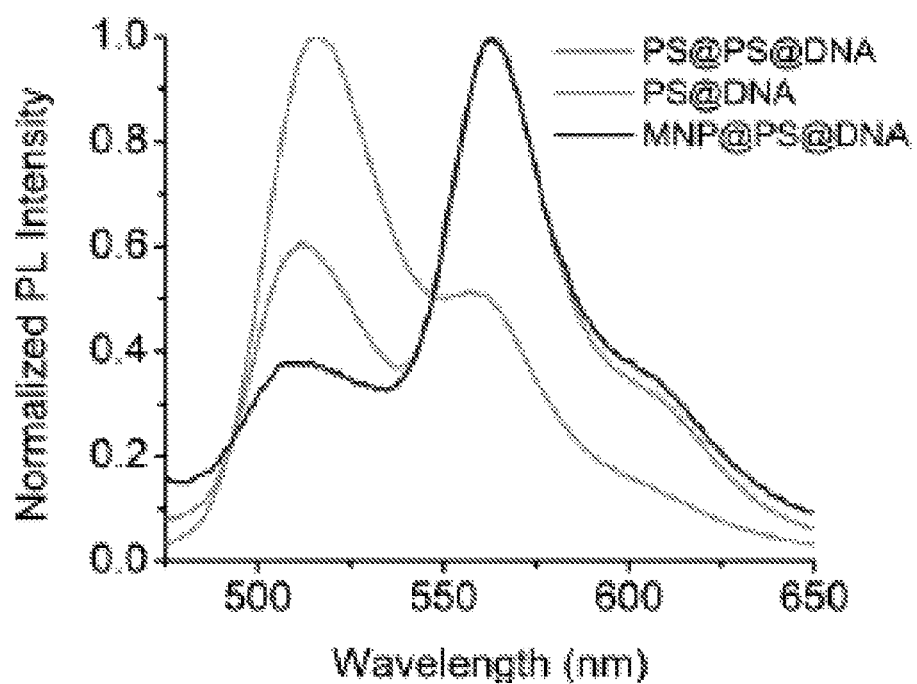
FIG. 7 shows photoluminiscent spectra of PS@PS@DNA (green) and PS@DNA micelles (orange) mixed with Cy3-labeled DNA in water at 20° C. Also shown is the spectrum of MNP@PS@DNA in the presence of Cy3-labeled DNA in water at 20° C. (blue) for comparison.

Surprisingly, Cy3-DNA binds to MNP@PS@DNA even at very low salt concentrations, as revealed by the increased Cy3 fluorescence intensity upon mixing MNP@PS@DNA and Cy3-DNA in water without added salts (FIG. 2C, solid). The $E_{FRET}$ for this solution was calculated to be 48.9±4.1%. Again, the FAM fluorescence intensity increases at high temperature due to the DNA dehybridization (FIG. 2C, dotted). When plain FAM-modified DNA was used instead of MNP@PS@DNA, Cy3 signal was negligible as expected, confirming that plain DNA strands do not form duplex at that condition (FIG. 2C, dashed). Moreover, the enhanced binding was also observed for large assemblies of DNA-b-PS encapsulating homopolymers of polystyrene 175±41 nm in diameter (PS@PS@DNA), but not for small simple DNA block-copolymer micelles (PS@DNA) with a diameter of 15±4 nm (FIGS. 6 and 7). These results reveal that the size of the assemblies, which directly correlates to the DNA density on the surface, is an importance factor in determining the DNA hybridization property. The densely packed DNA layer can increase the local DNA density and the local ion concentration, which are likely to be involved in the enhancement of DNA binding on the hybrid particles. The distinct behaviors of the hybrid assemblies and isolated DNA strands reveal that the high DNA density is responsible for the drastically enhanced binding capability.

Example 3

Binding Capability and Selectivity of MNP@PS@DNA

Figure 3:
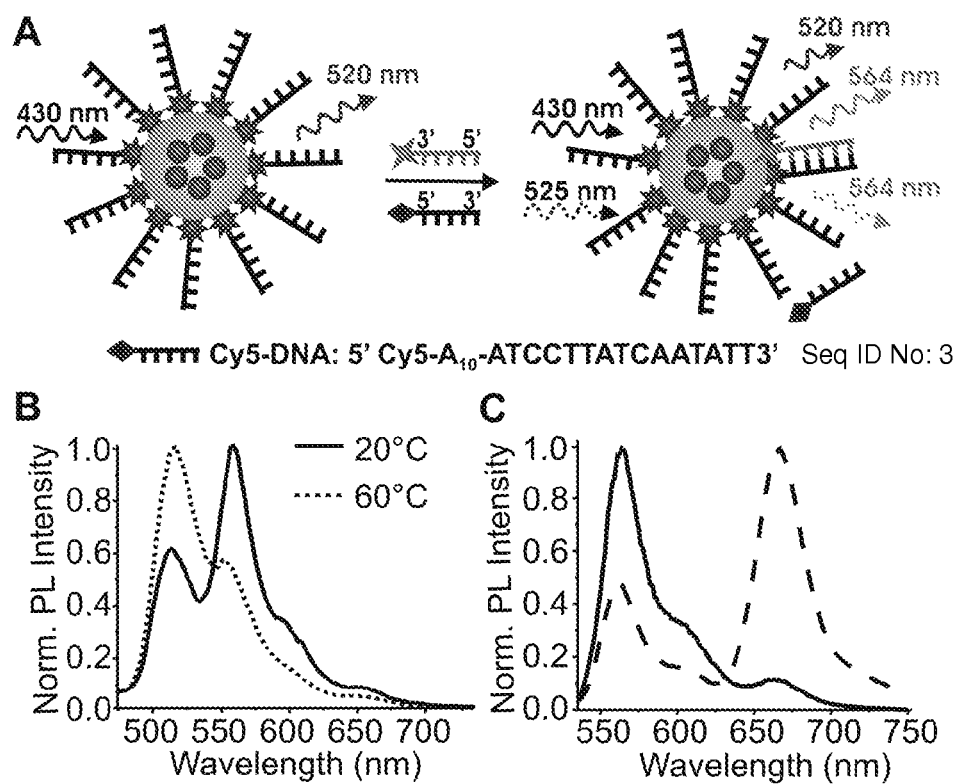
FIG. 3 shows (A) Schematic description for the preferential binding of Cy3-labeled target DNA to MNP@PS@DNA in the presence of Cy5-labeled competition DNA (i.e. plain DNA with same sequence as the DNA of MNP@PS@DNA). (B) Fluorescence spectra of the is competition experiment with MNP@PS@DNA, Cy3-labeled target strands (Cy3-DNA) and Cy5-labeled competition strands (Cy5-DNA), showing selective binding of target DNA to MNP@PS@DNA. $E_{FRET}$(FAM-Cy3)=36.0%. Excitation wavelength=430 nm. (C) Room temperature (20° C.) fluorescence spectrum of the competition experiment with 525 nm excitation (solid), confirming that competition Cy5-DNA strands exist as single stranded DNA ($E_{FRET}$(Cy3-Cy5)<1%). For comparison, fluorescence spectrum of Cy5-DNA and Cy3-DNA in 0.3 M PBS is also presented (dashed), which shows intense Cy5 emission via FRET, $E_{FRET}$(Cy3-Cy5)=74.7%.

The high binding capability of MNP@PS@DNA compared to isolated DNA strands was unambiguously demonstrated by a "competition experiment" (FIG. 3) where Cy5-modified DNA strands (Cy5-DNA: 5'Cy5-$A_{10}$-

ATCCTTATCAATATT3') (SEQ ID NO: 3) with the same sequence as the DNA in MNP@PS@DNA were mixed with Cy3-DNA and MNP@PS@DNA in water (FIG. 3A). In this scheme, the increase in Cy5 signal (668 nm) with 525 nm excitation indicates duplex formation between Cy3-DNA and Cy5-DNA, and the increase in Cy3 signal (564 nm) with 430 nm excitation indicates binding of Cy3-DNA to MNP@PS@DNA nanoparticles. FIG. 3B presents emission spectra collected at 430 nm excitation, which clearly showed hybridization between Cy3-DNA and MNP@PS@DNA. When excited at 525 nm, Cy3 emission was again dominant in the emission spectrum (FIG. 3C, solid), which indicated that Cy5-modified competition DNA (Cy5-DNA) did not bind to Cy3-modified target DNA (Cy3-DNA) at the condition. This competition experiment clearly shows that Cy3-DNA preferentially binds to MNP@PS@DNA when both MNP@PS@DNA nanoparticles and plain DNA of the same sequence are present.

Figure 4:
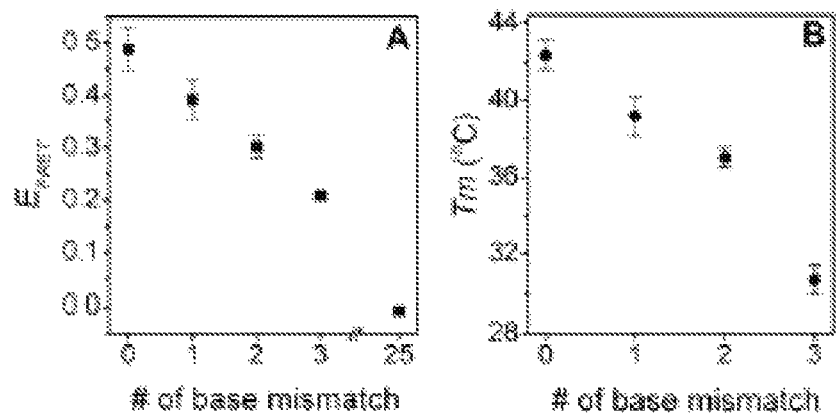
FIG. 4 shows FRET efficiencies ($E_{FRET}$) (A) and melting temperatures ($T_m$) (B) for DNA sequences with different numbers of base mismatches (underlined).
Figure 5:
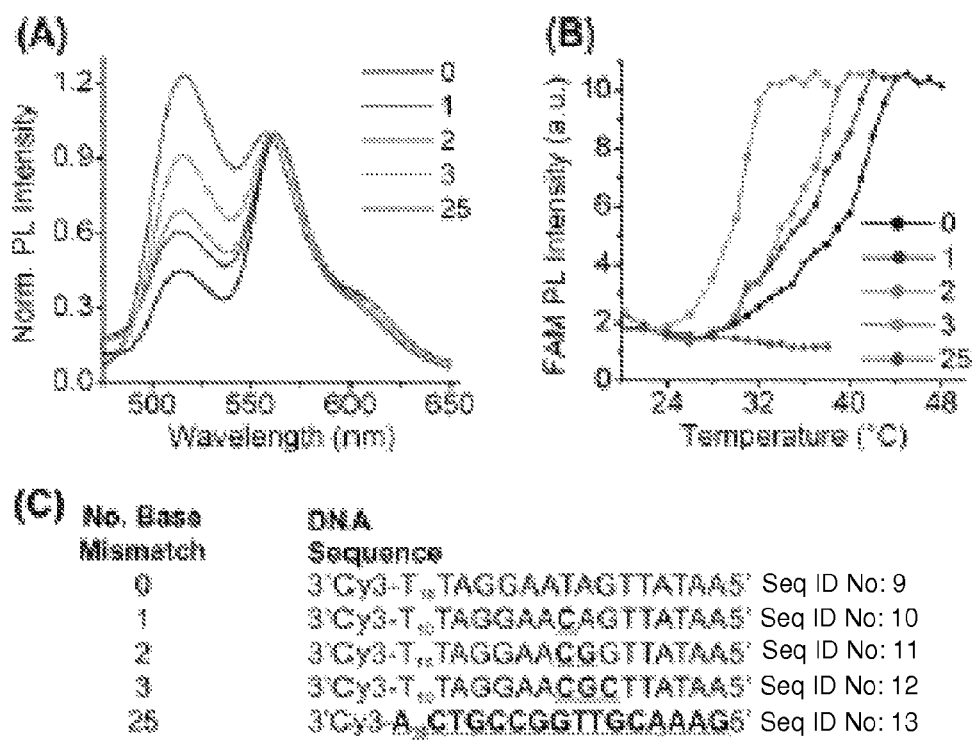
FIG. 5 shows (A) Photoluminescence spectra at 20° C. of MNP@PS@DNA solutions with DNA strands with different numbers of base mismatches. (B) Melting profiles of the same solutions in (A) constructed by monitoring the fluorescence intensity at 520 nm with increasing temperature. (C) DNA sequence used in the experiments.

Furthermore, these MNP@PS@DNA hybrid assemblies are highly selective in complementary DNA recognition and they can distinguish small numbers of base pair mismatches from the fully complementary sequence. To test the selectivity, DNA hybridization properties were measured for Cy3-modified DNA strands with 0, 1, 2, 3 base mismatches (FIGS. 4 and 5). The binding of fully noncomplementary DNA was also monitored for comparison. All experiments were carried out in water without added salt. The FRET efficiency and the melting temperature were determined for the mismatched DNA and presented in FIG. 4 along with the data for complementary DNA (Cy3-DNA). Both the FRET efficiency and melting temperature became progressively smaller with a larger number of base mismatches, and there was no detectable DNA binding for fully noncomplementary DNA. Notably, the FRET efficiency is significantly lowered even with one base mismatch, showing that the hybrid assemblies can distinguish a single base mismatch from fully complementary DNA sequence without any thermal treatment. This result also confirms that the DNA binding in the unusual condition (i.e., in purified water with no added salt) is due to sequence specific DNA interaction. Given that our MNP@PS@DNA can be used at very low salt concentrations where plain DNA exist as single stranded DNA, this hybrid material should be extremely effective in duplex DNA detection applications. The complementary sequence recognition at the very low ionic strength is a very unusual behavior due to the highly negatively charged phosphate backbone of DNA. Peptide nucleic acids (PNA) with neutral backbone have received significant attention for the capability to bind at low salt concentrations. While PNA suffers from the poor water solubility, our assemblies are stable in water over months without noticeable changes in the structure or binding properties. Furthermore, our DNA probes can be readily combined with nanoparticles and small molecules by self-assembly.

Example 4

Enhanced DNA Binding Property Induced by Ultra-High DNA Density in DNA Block Copolymer Assemblies We report here the origin of the observed enhanced binding of DNA block copolymer assemblies to be the result of an ultra-high DNA density on the surface of the assemblies. We have determined experimentally that the DNA density of the DNA block copolymer assemblies is more than four times higher than DNA-Au NP of the similar size. These assemblies clearly demonstrated a novel concept on bio-nanoparticles hybrid materials that has not been actively investigated, which is the properties of biomolecules in the bio-nanoparticle hybrid materials can be manipulated based on the local environment of the material to give rise to new properties. Moreover, these DNA block copolymer assemblies are shown to be ideal candidates for gene delivery applications, where they showed fast and efficient uptake by mammalian cells without the need of any secondary carrier agents, and the high DNA payload showed minimal degradation by nuclease.

Experimental

Preparation of DNA Block Copolymer Self Assemblies:
Synthesis of DNA block copolymer has been reported in detail previously. Briefly, the diblock copolymer was prepared using standard solid-state phosphoramidite chemistry, where phosphoramidite-terminated organic polymer was coupled to the oligionucleotides grown on glass beads. Simple micelles (Polymer@DNA): Simple micelles of DNA block copolymers were prepared by slow water addition to a solution of DNA block copolymer in dimethylforamide (DMF), follow by stiffing overnight and dialyzed for one day. Core filled micelles (X@Polymer@DNA; X=Polymer, Nanoparticles): Filling materials such as polymer and nanoparticles are dissolved in DMF and appropriate amounts of core filling materials was added to DNA block copolymer in DMF, follow by slow water addition. Diluent-strand assemblies: Assemblies with various percentage of diluent strands were prepared using diluent strands in DMF were mixed with the original DNA strands at corresponding ratios, appropriate amounts of core filling homopolymer was added to the solution. This was followed by slow water addition and dialyzed in water overnight.

Instruments:
Dynamic light scattering (DLS) hydrodynamic sizes of assemblies were measure using Malvent Instrument Zetasizer. The concentration of gold nanoparticles in a given solution of DNA block copolymer assemblies with encapsulated gold nanoparticles were measured using inductively coupled plasmon mass spectroscopy (ICP-MS). Thermal denaturation analyses monitored by UV-vis were carried out using Agilent UV-vis spectroscopy, thermal denaturation analyses monitored by the Förster resonance energy transfer (FRET) were performed using a FluorLog3 fluorimeter.

Cell Studie:
Instrument: Confocal microscopy was performed with an Olympics FV1000. HeLa cells culture: HeLa cells were cultured with phenol red-free Dulbecco's modified Eagle's medium (DMEM) supplemented with 10% fetal bovine serum (FBS) in 75 mL cell culture flaks at 37° C. with 5% $CO_2$ and 95% relative humidity. The cells were split and seeded every three to four days.

Results:
Size Dependence of Enhanced DNA Binding:
We have shown that DNA block copolymer self-assemblies with encapsulated magnetic nanoparticles (MNP @PS@DNA) exhibit enhanced DNA binding properties, where they can hybridize with complementary DNA strands with high selectively in solutions with extremely low salt concentrations, a condition in which free DNA strands do not hybridize. It was the first to report enhanced DNA properties of this kind. Based on the expected structure of the assemblies, we speculated that there are two possible origins for this enhanced binding: 1. the presence of dyes and 2. the high density of DNA strands on the assembly surface.

Figure 8:
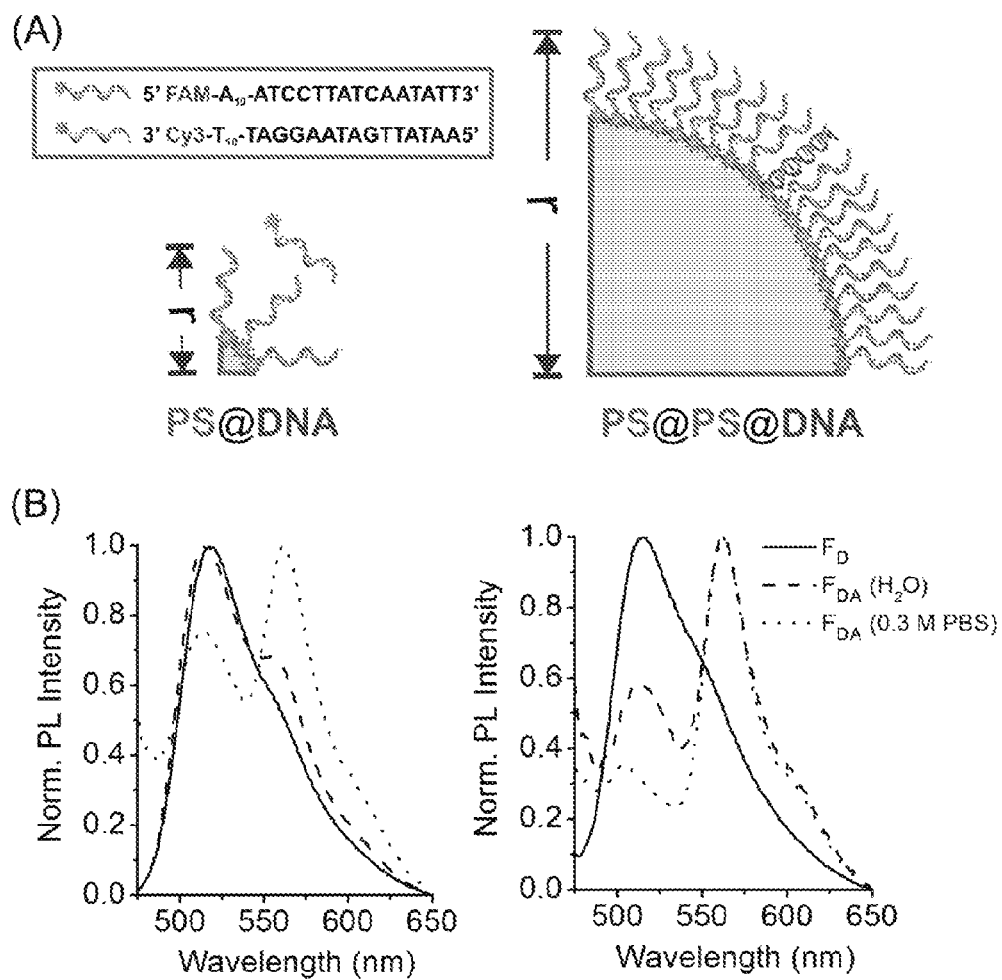
FIG. 8 shows: (A) Scheme of PS@DNA and PS@PS@DNA SEQ ID NOs: 1 and 2, showing how the radius of curvature affect the number of strands can pack on the assemblies; and (B) PL of PS@DNA and PS@PS@DNA assemblies in the absences of acceptor ($F_D$) and in the presences of acceptor ($F_{DA}$) in solutions with no added salt and in 0.3 M PBS.

We have found that this enhanced DNA binding property can be extended to any DNA block copolymer self-assemblies with nanoparticles or homopolymers encapsulated in the core of the assemblies, typical size of 100 to 150 nm, FIG. 8b. Shown in FIG. 8b are emission spectra of assemblies prepared from fluorescein (FAM)-labeled DNA block copolymer alone ($F_D$) or in the presence of an acceptor ($F_{DA}$), in this case the acceptors are Cy3-labeled complementary DNA, and the hybridization process was monitored by Förster energy transfer between FAM and Cy3. Interestingly, self-assemblies without core-fillings, i.e. simple micelles with typical size of 15 nm, do not show this enhanced binding property as shown in FIG. 8b which showed no FRET from FAM to Cy3. This size dependency is attributed to the difference in the number of DNA on the surface of the assemblies as a result of their radius of curvature (FIG. 8a), where it is expected the simple micelles have less number of DNA on the surface of the assemblies compared to the larger assemblies, FIG. 8a. Also shown for comparison in FIG. 8b are emission spectra of the two different size FAM-labeled assemblies hybridized with Cy3-labeled target at 0.3M PBS when there is FRET, thus when there is hybridization.

Concentration Dependent Thermal Dynamic Analysis:

Thermal dynamic analysis of the DNA block copolymer assemblies with homopolymer filled core (PS@PS@DNA), simple DNA block copolymer micelles (PS@DNA) and free DNA strands showed the differences in the thermodynamic parameters of the three species (Table 1). The thermodynamics parameters were extracted from concentration dependent binding studies using van't Hoff's equation. In general, DNA binding by PS@PS@DNA is stronger than that of PS@DNA and plain DNA strands.

$$\frac{1}{T_m} = \frac{R}{\Delta H^\circ}\ln C_T + \frac{\Delta S^\circ - R\ln 4}{\Delta H^\circ}$$

Figure 9:
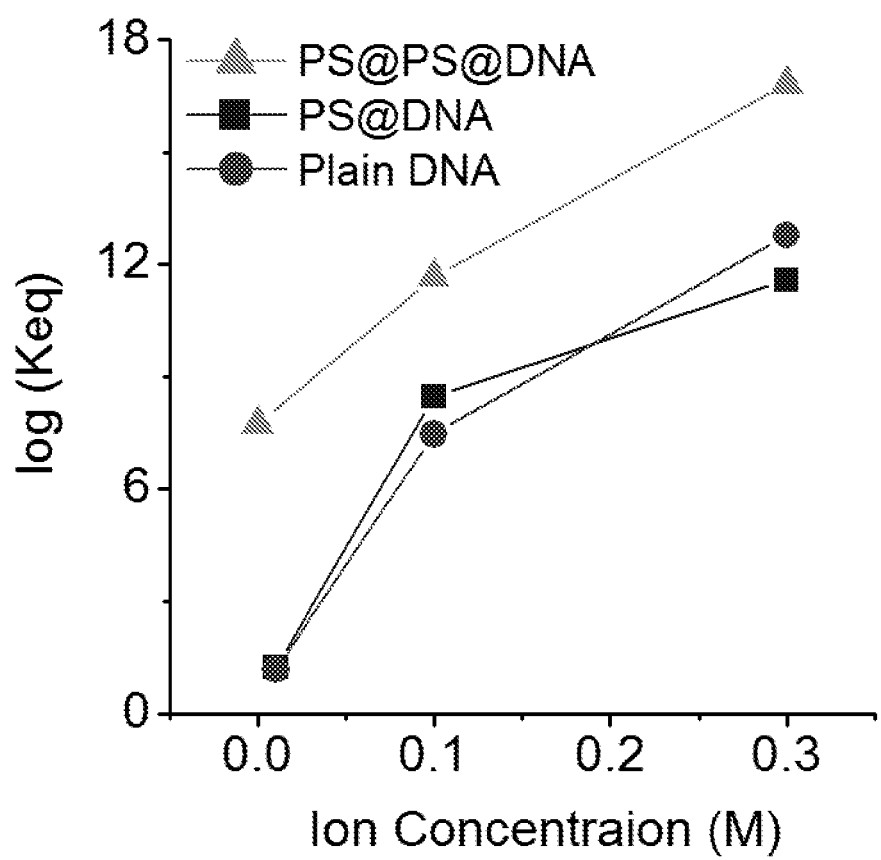
FIG. 9 shows Kbind of plain DNA, DNA block copolymer assemblies of simple micells (PS@DNA) and homopolymer fillied assemblies (PS@PS@DNA) at different salt conditions.

Thermodynamic analyses were carried out at three different salt concentrations, 0M, 10 mM and 300 mM NaCl. Thermodynamic parameters (enthalpy, entropy, Gibb's free energy and binding constants) determined from the concentration dependent thermal dynamic analysis showed that the DNA binding capability of DNA block copolymer assemblies with filled cores was less sensitive to salt concentrations in the solution. Where in solutions with no added salt when plain DNA strands do not form duplex, and overall the PS@PS@DNA assemblies showed a binding constant that is higher than plain DNA strands in any salt concentrations, FIG. 9.

TABLE 1

Thermodynamic parameters (delta H, S, G and Kbind of plain DNA, PS@NDA and PS@PS@DNA.
Table 1: Thermodynamic Values of Plain DNA and DNA Block Copolymer Assemblies PS@DNA and PS@PS@DNA.

| Ion Concentration | ΔH° (kcal/mol) | ΔS° (cal/mol · K) | ΔG° (kcal/mol) |
|---|---|---|---|
| Plain DNA | | | |
| 10 mM | −0.30 | 4.4 | −1.6 |
| 100 mM | −18.8 | −28.8 | −10.2 |
| 300 mM | −102.6 | −286.5 | −17.4 |
| PS@DNA | | | |
| 10 mM | −1.53 | 0.58 | −1.7 |
| 100 mM | −31.6 | −67.4 | −11.5 |
| 300 mM | −105.4 | −300.3 | −15.8 |
| PS@PS@DNA | | | |
| 0M | −17.5 | −25.2 | −10.1 |
| 100 mM | −80.3 | −217.3 | −15.6 |
| 300 mM | −127.0 | −350.2 | −22.6 |

Figure 10:
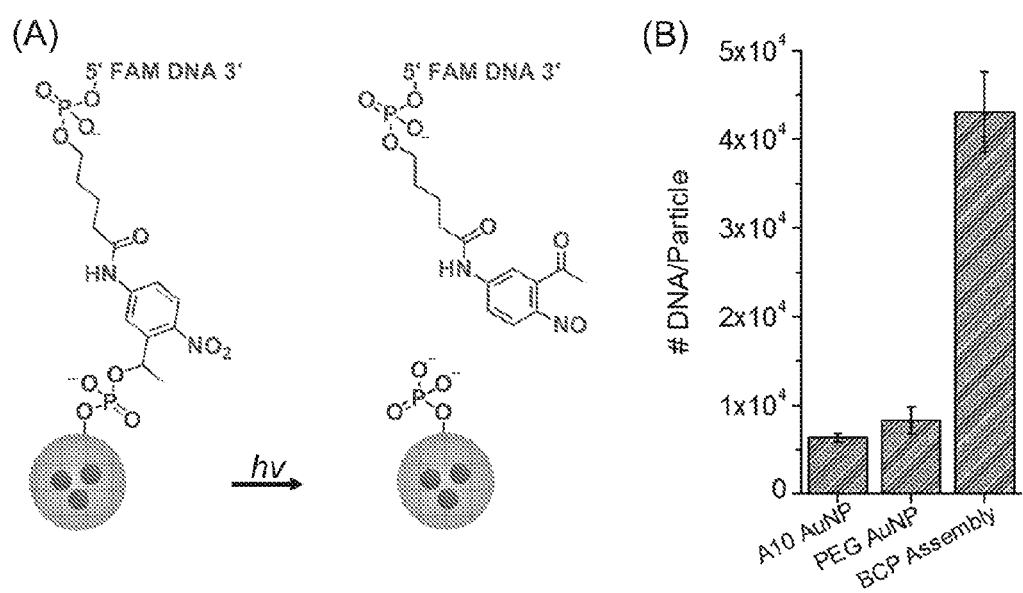
FIG. 10 shows: (A) Scheme of photocleavable DNA and process to determine the number of strands using PL and (B) Plot of number of DNA strands per DNA block copolymer assembly (BCP assembly) and number of DNA strands per DNA functionalized gold nanoparticles (AuNP) with A10 and PEG spacer at maximized loading.

Surface DNA Density:

The number of DNA strands per assembly was determined using dye-labeled photocleavable strands (FIG. 10). Gold nanoparticles were used as markers to indicate the number of assemblies in a given solution. Detailed experimental procedures for the determination of the number of assemblies in a given solution can be found in the supporting information. The average number of DNA strands per assembly was determined based on the total number of cleaved DNA strands in solution over the total number of assemblies in a given solution. The DNA block copolymer assemblies with encapsulated gold nanoparticles (Au@PS@DNA) used were analyzed and confirmed that they possess the same physical properties as the other DNA block copolymer assemblies, that is these assemblies are similar in size and shape (supporting information) and they also displayed the enhanced binding at extremely low salt concentrations.

The DNA density of Au@PS@DNA was determined to be around 80 pmol/cm$^2$, more than four times higher than the maximized DNA loading value of the DNA-functionalized gold nanoparticles of the same size with A10 spacers (15 pmol/cm$^2$). The number of DNA strands per assembly exceeds that of DNA-Au NP with the highest functionalization value 19 pmol/cm$^2$. This DNA density is the highest reported in the literature for DNA conjugated nanoparticles.

Figure 11:
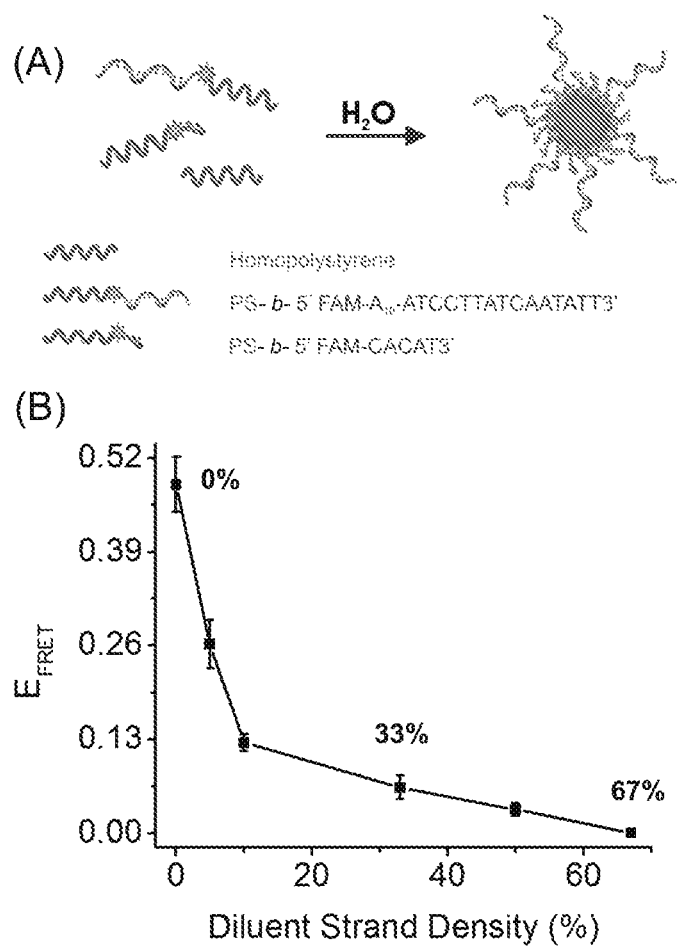
FIG. 11 shows: (a) Scheme of dilution (show strand sequence SEQ ID NO: 1) and (b) plot of ratio of dilution versus FRET efficiency

"Diluent" Strands:

The ultra-high DNA density was determined to play a crucial role in the observed enhanced binding as demonstrated using "diluent" strand experiments. Where "diluent" strands were short DNA strands with a random sequence used to dilute the DNA density on the surface of the assemblies (FIG. 11a).

As the diluent strand ratio was increased gradually, we observed a drastic decrease in the binding affinity as illustrated in the sharp decrease in the FRET efficiency in solutions with no added salt at as little as 5% of diluent strands in the assembly.

The other possible factor that could have contributed to the observed enhanced binding was the presences of the dye molecules, given the aromatic structure of the dyes, there could be favorable interactions between the dyes with the bases in the DNA. To determine the possibility of interaction, we also performed a similar diluent experiment for the dilution of dyes on the surface of the assemblies, and found that the dilution of dyes does not affect the FRET efficiency.

Cellular Uptake Studies:

A recent study showed that the high local salt concentrations induced by the high DNA density of DNA functionalized gold nanoparticles selectively deactivates the binding capability of DNAse I while enhances the activity of RNAseH.

Figure 12:
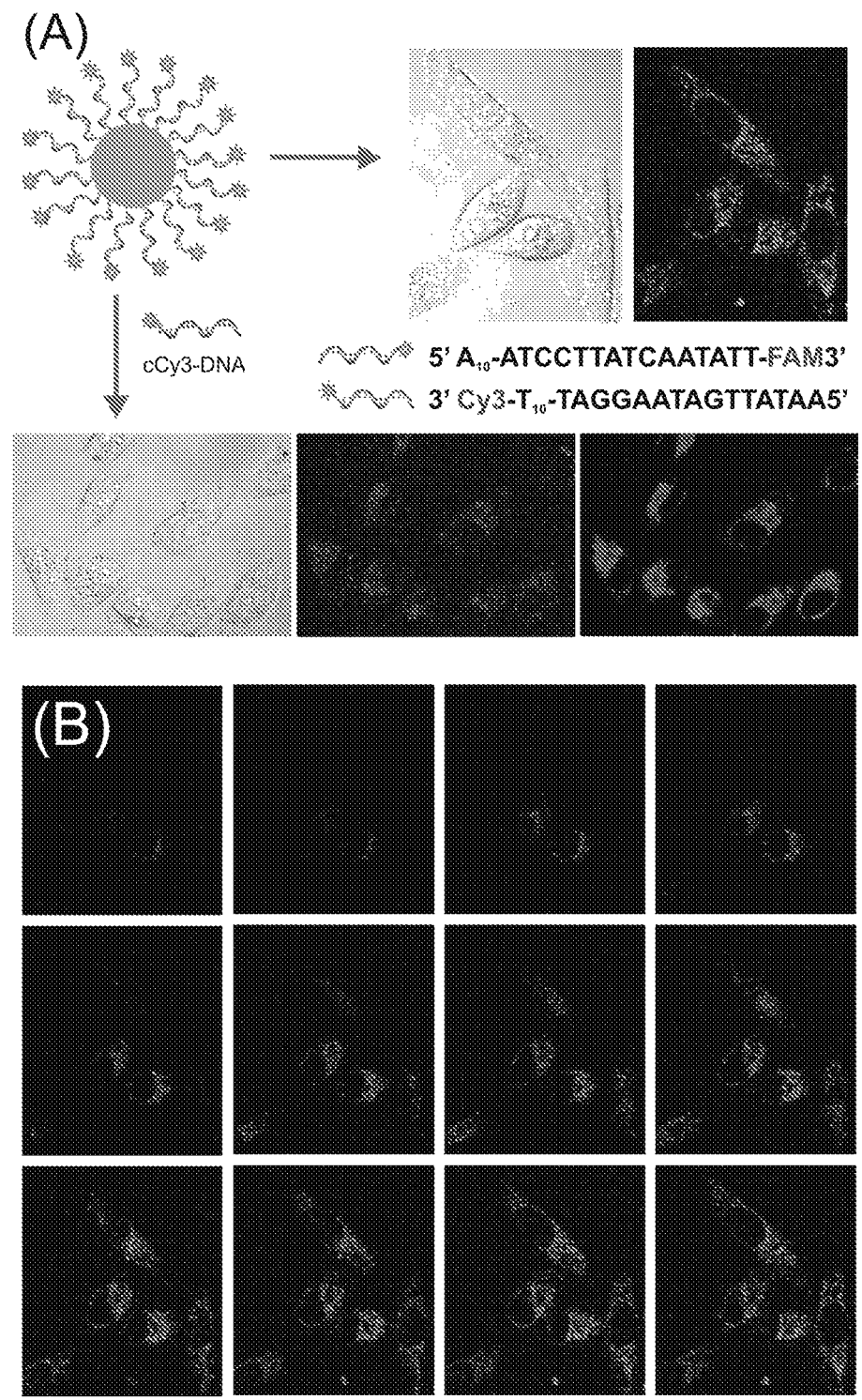
FIG. 12 shows confocal images of HeLa cells: (A) top, after incubation with PS@PS@FAM-DNA; bottom, and PS@PS@FAM-DNA hybridized with complementary Cy3-DNA SEQ ID NOs: 1 and 2, and (B) z-sectioning images of cells incubated with PS@PS@FAM-DNA, section size=2 microns. FAM: fluorescein, Cy3: cyanine dye.

Cellular uptake studies using PS@PS@DNA assemblies showed efficient uptake using HeLa cells, where by fluorescent microscopy>99% of cells show fluorescence from the dye-labeled DNA block copolymer assemblies. Cellular studies with DNA block copolymer assemblies with homopolymer fillers (PS@PS@DNA, using the PC DNA BCP strands with dye at 3' end) in the core demonstrated effective uptake by mammalian cells, FIG. 12a. Moreover, duplexed DNA strands with Cy3-target DNA strands (FIG. 12b) clearly demonstrated that there is no DNA degradation by DNAse as indicated DNA strands are intact. This shows that these ultra-high DNA density assemblies are promising gene delivery agents.

In summary, we have determined that DNA block copolymer assemblies with fillers (nanoparticles or homopolymers) in the core possessed ultra-high DNA density on the surface, more than four times higher than the highest reported value in the literature. We have determined that this ultra-high DNA density is critical for enhanced DNA binding exhibited by these DNA block copolymer assemblies. As illustrated by diluent strands experiments, where with the gradual diluent of the DNA strands on the surface while keeping the structure constant showed a drastic decrease in the DNA binding affinity of these assemblies with the target strands at extremely low salt conditions, and this enhanced binding almost completely disappeared for assemblies with 50% of diluent strands in the composition.

We have also demonstrated that these ultra-high DNA block copolymers to be effective gene delivery agent, where the ultra-high DNA density helped protect the DNA cargo from DNA degradation by DNAse, enabling a high pay load delivery per assembly, the highest reported for synthetic delivery systems.

Example 5

Gene Regulation in Cells Using Antisensing DNA Block Copolymer Assemblies

We have recently demonstrated the following using core-filled DNA block copolymer assemblies (i.e. assemblies with encapsulated homopolymer or nanoparticles in their hydrophobic cores): (1) Efficient cellular uptake of homopolymer filled DNA block copolymer assemblies (PS@PS@DNA) into HeLa cells (FIG. 12), and 2) these assemblies also showed significant antisensing activity, i.e. down regulation capability, when the DNA block contains the antisensing sequence for green fluorescent protein (GFP) in GFP transfected HeLa cells. (FIG. 13).

Cellular uptake studies of the antisensing DNA block copolymer assemblies were performed using HeLa cells with fluorescein (FAM) tagged PS@PS@DNA. As shown in the top confocal image in FIG. 12a, the assemblies appeared to be evenly distributed inside the HeLa cells, sparing the nucleus, and this was confirmed by z-section confocal images, FIG. 12b. Assemblies with two dyes, FAM tagged PS@PS@DNA hybridized with Cy3-labeled target strands, were also used to determine the degradation of the DNA payload. Confocal images on the bottom of FIG. 12a showed the presence of both dyes inside cells, indicating that the strands are intact inside cells.

Figure 13:
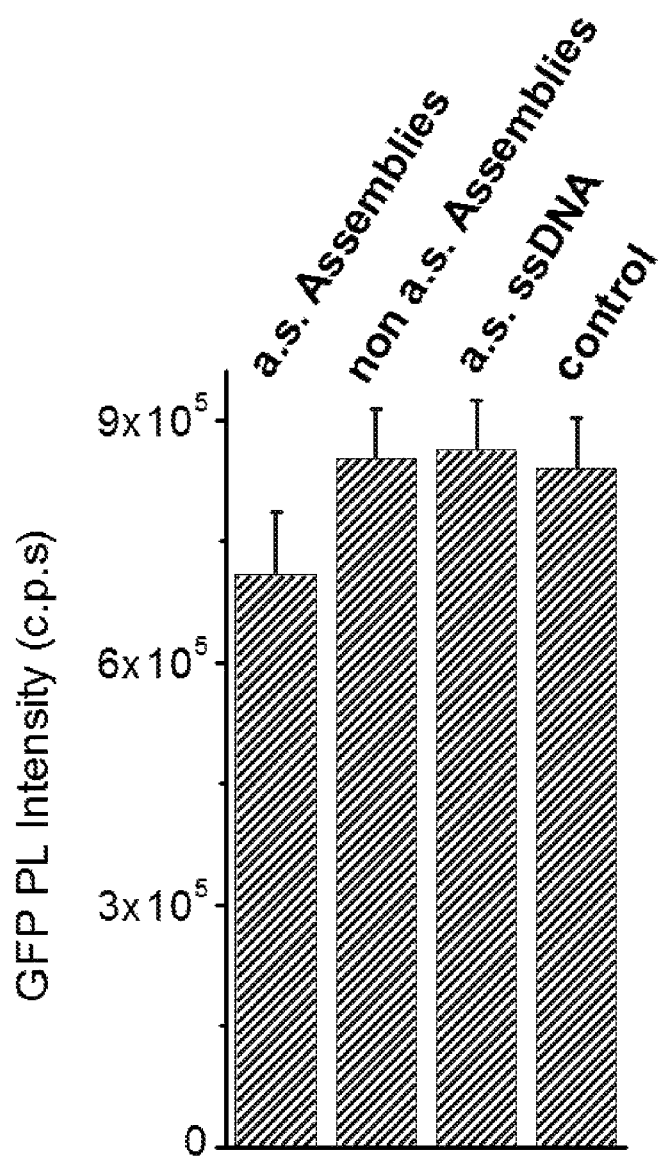
FIG. 13 shows plots of emission intensity of green fluorescent proteins (GFP) in GFP-transfected HeLa cells with DNA block copolymer assemblies containing antisensing sequence (a.s. Assemblies). Also of assemblies with non-antisensing sequence (non a.s. Assemblies) and antisensing single-stranded DNA (a.s. ssDNA) and control with pristine GFP-transfected HeLa cells (control).

Finally, we were able to demonstrate down regulation of green fluorescent protein (GFP) in GFP-transfected HeLa cells using antisensing DNA block copolymer assemblies, FIG. 13. HeLa cells treated with antisensing DNA block copolymer assemblies showed a significant decrease in the emission intensity of GFP. Assemblies with scrambled DNA strands as well as the antisensing DNA alone do not show this down regulation.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

---

What is claimed is:

1. A nanoparticle-nucleic acid hybrid structure, comprising a high density oligonucleotide-amphiphilic block co-polymer exterior assembly and a hydrophobic nanoparticle core.

2. The hybrid structure of claim 1, wherein said nucleic acid is DNA, RNA, artificial nucleic acids or a combination thereof.

3. The hybrid structure of claim 1, wherein said oligonucleotide is an oligonucleotide ranging in size from 5-100 base pairs.

4. The hybrid structure of claim 1, wherein said block-copolymers comprise an oligonucleotide block and a polystyrene block.

5. The hybrid structure of claim 1, wherein said structure enables detection of single base mismatches from complementary strands.

6. The hybrid structure of claim 1, wherein said structure enhances its stability in water.

7. The hybrid structure of claim 6, wherein said nanoparticle is an iron oxide magnetic particle.

8. The hybrid structure of claim 1, wherein said nanoparticle is a gold nanoparticle, a magnetic nanoparticle, a semiconductor nanoparticle, an insulator nanoparticle, a metallic nanoparticle, a carbon black particle, a quantum dot or any combination thereof.

9. The hybrid structure of claim 8, wherein said iron oxide magnetic particle is functionalized via ligand exchange with alpha-carboxyl polystyrene.

10. The hybrid structure of claim 1, wherein the nanoparticle is a magnetic nanoparticle selected from the group consisting of a metal nanoparticle, a metal oxide nanoparticle, a metalloid nanoparticle, a metalloid oxide nanoparticle, or a combination thereof.

11. The hybrid structure of claim 1, wherein said nanoparticle ranges in size from 1-1000 nanometers in diameter.

12. The hybrid structure of claim 1, wherein said structure enables selective nucleic acid binding to complementary nucleic acid under low salt concentration.

13. The hybrid structure of claim 1, wherein said structure enhances the binding affinity to a nucleic acid complementary to said nucleic acid.

14. The hybrid structure of claim 1, wherein said nucleic acid on said structure selectively binds to a complementary nucleic acid by detecting mismatches between said nucleic acid on said hybrid structure and a nucleic acid contacted by said hybrid structure.

15. The hybrid structure of claim 14, wherein said fluorescence molecule is a fluorescein, a cyanine dye, or a combination thereof.

16. The hybrid structure of claim 1, wherein said structure further comprises a fluorescence molecule.

17. A method for facilitating self-assembly of a nanoparticle-nucleic acid hybrid structure, comprising a high density oligonucleotide-amphiphilic block co-polymer exterior assembly and a hydrophobic nanoparticle core, the method comprising the step of mixing a pre-determined amount of nucleic acid amphiphilic block-copolymer with a pre-determined amount of nanoparticles to facilitate the self-assembly of said hybrid structure.

18. A method for transfecting a cell with a nucleic acid, comprising contacting a cell with a nanoparticle-nucleic acid hybrid structure, comprising a high density oligonucleotide-amphiphilic block co-polymer exterior assembly and a hydrophobic nanoparticle core.

19. The method of claim 18, wherein the hybrid structure further comprises a targeting agent.

20. The method of claim 19, further comprising contacting the cell with the hybrid structure in the presence of an applied magnetic field.

21. A method of separating nucleic acid molecules, said method comprising the step of contacting a nucleic said molecule complementary to said nucleic acid molecule comprised by a nanoparticle-nucleic acid hybrid structure, comprising a high density oligonucleotide-amphiphilic block co-polymer exterior assembly and a hydrophobic nanoparticle core.

22. The method of claim 21, further comprising the step of contacting the nucleic acid with the hybrid structure in the presence of an applied magnetic field.

23. A method for imaging a cell, comprising: contacting a cell with a nanoparticle-nucleic acid hybrid structure to provide a labeled cell, wherein said nanoparticle-nucleic acid hybrid structure comprises a high density oligonucleotide-amphiphilic block co-polymer exterior assembly and a hydrophobic nanoparticle core; and imaging the labeled cell.

24. The method of claim 23, wherein imaging comprises optical imaging, wherein said optical imaging is fluorescence imaging, scattering imaging, colorimetric imaging, electron microscopy imaging, or magnetic resonance imaging.

25. The method of claim 23, wherein the hybrid structure comprises a quantum dot and the imaging comprises fluorescent imaging.

26. The method of claim 23, wherein the hybrid structure comprises a magnetic nanoparticle and the imaging comprises magnetic resonance imaging.

27. The method of claim 23, wherein the hybrid structure further comprises a targeting agent.

28. A method for detecting a complementary nucleic acid sequence with high selectivity, the method comprising the step of utilizing a nanoparticle-nucleic acid hybrid structure in an assay to selectively detect said complementary nucleic acid, wherein said nanoparticle-nucleic acid hybrid structure comprises a high density oligonucleotide-amphiphilic block co-polymer exterior assembly and a hydrophobic nanoparticle core.

29. The method of claim 28, wherein said selection process is a nucleic acid binding assay that detects binding of said nucleic acid to a complementary nucleic acid.

30. The method of claim 28, wherein said hybrid structure enables detection of a complementary nucleic acid under low salt concentrations.

31. The method of claim 28, wherein said complementary nucleic acid sequence is a sequence of a gene.

32. A method for delivering a composition to a cell, the method comprising: contacting said cell with a nanoparticle-nucleic acid hybrid structure that comprises a high density oligonucleotide-amphiphilic block co-polymer exterior assembly and a hydrophobic nanoparticle core.

33. A nanoparticle-nucleic acid hybrid structure, comprising a high density oligonucleotide-amphiphilic block co-polymer exterior assembly and a hydrophobic nanoparticle core, wherein said hybrid structure comprises more oligonucleotides than a structure having said nanoparticle alone without said oligonucleotide-amphiphilic block co-polymer exterior assembly.

* * * * *